United States Patent [19]

Millauer et al.

[11] Patent Number: 5,767,333

[45] Date of Patent: Jun. 16, 1998

[54] PROCESS FOR PREPARING 2,2'-DIMETHYL-1,1'BINAPHTHYL AND 2,7'-DIMETHYL-1,1'-BINAPHTHYL

[75] Inventors: Hans Millauer, Eschborn; Adolf Schmidt, Hofheim, both of Germany

[73] Assignee: Hoechst AG, Germany

[21] Appl. No.: 351,609

[22] Filed: Dec. 8, 1994

[30] Foreign Application Priority Data

Dec. 11, 1993 [DE] Germany ............... 43 42 282.9
Apr. 19, 1994 [DE] Germany ............... 44 13 616.1

[51] Int. Cl.$^6$ ............... C07C 2/02; C25B 3/10
[52] U.S. Cl. ............... 585/425; 205/415; 205/419; 205/462; 205/463
[58] Field of Search ............... 585/425; 205/415, 205/419, 462, 463

[56] References Cited

U.S. PATENT DOCUMENTS 4,458,047  7/1984  Vanderwerff ............... 585/425
5,510,554  4/1996  Regnat et al. ............... 585/466
5,522,982  6/1996  Brietzke et al. ............... 205/413

OTHER PUBLICATIONS

European Search Report No. 94118413.7 –May 29, 1995.

Electro–Oxidation of 2–Methylnaphthalene in Aqueous Acetonitrile. Department of Industrial Chemistry. Niihama National College of Technology. Niihama, 792 Japan 1989 (No Month).

*Primary Examiner*—Walter D. Griffin
*Attorney, Agent, or Firm*—Connolly & Hutz

[57] ABSTRACT

2.7'-Dimethyl-1,1'-binaphthyl and a process for preparing 2,2'-dimethyl-1,1'-binaphthyl and 2,7'-dimethyl-1,1'-binaphthyl by electrochemically oxidatively dimerizing 2-methylnaphthalene in the presence of acetonitrile/water/electrolyte salt mixtures which additionally contain at least one further component which, is immiscible or only partially miscible with water, and rectifying the reaction mixture obtained under reduced pressure.

45 Claims, No Drawings

PROCESS FOR PREPARING 2,2'-DIMETHYL-1,1'BINAPHTHYL AND 2,7'-DIMETHYL-1,1'-BINAPHTHYL

BACKGROUND OF THE INVENTION (i) Field of the Invention

The present invention relates to 2,7'-dimethyl-1,1'-binaphthyl and a process for preparing 2,2'-dimethyl-1,1'-binaphthyl and 2,7'-dimethyl-1,1'-binaphthyl by anodic coupling of 2-methylnaphthalene using special electrolyte systems.

(ii) Description of the Related Art

Dimethyl-1,1'-binaphthyls are intermediates for the preparation of phosphorus-containing ligands of catalytically active rhodium complexes. These compounds are used in industrial processes as catalysts (binas/naphos catalysts) for the oxo synthesis.

The preparation of 2,2'-dimethyl-1,1'-binaphthyl by a chemical route is carried out by reductive coupling of 1-bromo-2-methylnaphthalene which is obtained by bromination of 2-methylnaphthalene. For this purpose, 1-bromo-2-methylnaphthalene is converted into the corresponding Grignard compound and subsequently coupled with 1-bromo-2-methylnaphthalene using a nickel-containing catalyst, for example $Ni(PPh_3)_2Cl_2$. The yield based on the 2-methyl-naphthalene used is, calculated over both steps, from about 50 to 60%. In addition, the process gives, as production waste, a mixture of magnesium bromide and nickel salts which have to be separated and worked up (S. Miyano, Bull. Chem. Soc. Jpn., 59, (6), 2044 to 2046, 1986).

K. Tabuchi et al., Memoirs of the Niihama College of Technology Science and Engineering, 25, 58 (1989) describe the potential-controlled electrooxidation of 2-methylnaphthalene in aqueous acetonitrile or acetone. The products obtained here include up to 33.4% of "dimer" which is said to be the uniform compound 2,2'-dimethyl-1,1'-binaphthyl and approximately equal amounts of "polymers" besides smaller amounts of 2-methyl-1,4-naphthoquinone.

The above-described method is, in terms of an industrially usable production process, unsatisfactory because of the yield which can be achieved. In repeating the work of the literature reference cited above, it was additionally established that the product described as "dimer" comprises a mixture of at least 5 isomeric dimethyl-binaphthyls containing about 50% of the compound 2,2'-dimethyl-1,1'-binaphthyl. Furthermore, it has been found that the high proportion of polymers results in the formation of covering layers on the electrodes, which considerably hinder the electrosynthesis (Comparative Example 19).

2,7'-Dimethyl-1,1'-binaphthyl or a process for the preparation thereof have not yet been described.

Owing to the general importance and the wide usability of this class of materials, it is a worthwhile object to prepare this new representative of the group of dimethyl-1,1'-binaphthyls, so as to not only supplement the range of their possible applications, but also to enrich and expand material properties by means of subtle changes.

There has therefore been a great need for a process which enables 2,2'-dimethyl-1,1'-binaphthyl and 2,7'-dimethyl-1,1'-binaphthyl to be obtained in high yield and purity.

SUMMARY OF THE INVENTION

This object is achieved by a process for preparing 2,2'-dimethyl-1,1'-binaphthyl and 2,7'-dimethyl-1,1'-binaphthyl, which comprises electrochemically oxidatively dimerizing 2-methylnaphthalene in the presence of acetonitrile/water/electrolyte salt mixtures which additionally contain at least one further component which is immiscible or only partially miscible with water, and rectifying the reaction mixture obtained under reduced pressure.

DESCRIPTION OF THE PREFERRED EMBODIMENTS

The process is based on the oxidative (anodic) dimerization of 2-methylnaphthalene and proceeds in accordance with the following reaction equation:

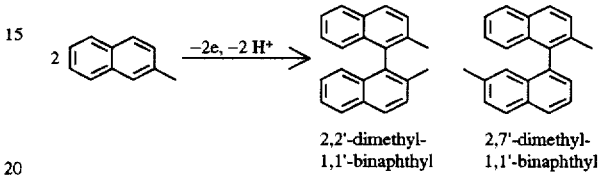

2,2'-dimethyl-1,1'-binaphthyl    2,7'-dimethyl-1,1'-binaphthyl

The electrolyte systems used for the process of the invention can be formed in various ways. However, in principle, the composition of such electrolyte systems always includes acetonitrile, water, an electrolyte salt and at least one further component which is immiscible or only partially miscible with water.

The water-immiscible component can be (a) an aliphatic or cycloaliphatic hydrocarbon such as, for example, pentane, hexane, cyclohexane, methylcyclohexane, heptane, octane, isooctane, decane, dodecane or decalin or mixtures (distillation fractions) of such compounds, or (b) an aromatic hydrocarbon such as, for example, benzene, toluene, o-, m-, or p-xylene, mesitylene, naphthalene or tetralin, or (c) a halogenated hydrocarbon such as, for example, methylene chloride or chlorobenzene, or (d) a ketone having from about 5 to 10 carbon atoms such as, for example, diethyl ketone, methyl t-butyl ketone or acetophenone.

Preference is given to using aliphatic, cycloaliphatic or aromatic hydrocarbons having from 6 to 10 carbon atoms; particular preference is given to heptane, octane, toluene and xylene.

The water-immiscible component can also be 2-methylnaphthalene itself; in this case, i.e. for those electrolytes which contain none of the above-mentioned components, it is a condition that the amount of 2-methylnaphthalene used is calculated in such a way that a 2-methylnaphthalene concentration of at least 10%, based on the total weight of the electrolyte, is always present during electrolysis.

The water-immiscible component of the electrolyte system can also be a mixture of two or more of the above-mentioned compounds.

Suitable electrolyte salts for the process of the invention are the alkali metal, alkaline earth metal, ammonium, monoalkylammonium, dialkylammonium, trialkylammonium or tetraalkylammonium salts of acids whose complex anions are derived from 6-valent sulfur, from 5-valent phosphorus or from 3-valent boron. Mixtures of various ones of the electrolyte salts specified can likewise be used.

Salts which can be used are, for example, the salts of the following anions, hydrogen sulfate, methyl sulfate, ethyl sulfate, methanesulfonate, ethanesulfonate, propanesulfonate, butanesulfonate, octanesulfonate, benzenesulfonate, toluenesulfonate, 2-chlorobenzenesulfonate, p-chlorobenzenesulfonate, 2,4-dichlorobenzenesulfonate, naphthalene-1-sulfonate, naphthalene-2-sulfonate; methanephosphonate, ethanephosphonate, propanephosphonate, butanephosphonate, hexafluorophosphate; tetrafluoroborate; further suitable salts are those of alkanesulfonic acids or alkanephosphonic acids whose alkyl radical is polyfluorinated or perfluorinated, such as, for example, trifluoromethanesulfonate, 1,1,2,3,3,3-hexafluoropropanesulfonate, nonafluorobutanesulfonate, heptadecafluorooctanesulfonate, trifluoromethanephosphonate, nonafluorobutanephosphonate.

In many cases it has been found to be useful to use sodium or tetraalkylammonium salts (having alkyl radicals containing from 1 to 4 carbon atoms) of alkanesulfonic acids (having alkyl radicals containing from 1 to 8 carbon atoms or having polyfluorinated or perfluorinated alkyl radicals containing from 1 to 4 carbon atoms), of arylsulfonic acids (having aryl=phenyl, naphthyl; alkyl-substituted or chloro-substituted phenyl), of tetrafluoroboric acid and of hexafluorophosphoric acid as electrolyte salts.

The ratio of acetonitrile to water is, in the electrolytes used in the range from 100:1 to 1:1; it has been found to be favorable to work in the range from 20:1 to 2:1. The amount of the component which is immiscible or only partially miscible with water is, based on the total weight of the electrolyte, in the range from 10% to 90%; preference is given to the range from 20 to 80%.

The amount of electrolyte salt is, based on the total weight of the electrolyte, in the range from 0.5% to 15%; preference is given to the range from 1 to 7%.

Preferred ratios for the electrolyte components are those which lead to two-phase electrolyte systems. For example, electrolyte systems which are composed of acetonitrile, water, heptane, electrolyte salt and 2-methylnaphthalene in such ratios that a phase consisting mostly of water, acetonitrile and electrolyte salt and also a part of the 2-methylnaphthalene and a phase consisting mostly of heptane and the remaining methylnaphthalene are present; or, for example, electrolyte systems which are composed of acetonitrile, water, toluene, electrolyte salt and 2-methylnaphthalene in such ratios that a phase consisting mostly of water and a part of the electrolyte salt and a phase consisting mostly of acetonitrile, toluene, remaining electrolyte salt and 2-methylnaphthalene are present.

The process is carried out in an undivided electrolysis cell. For larger-scale electrolyses, preference is given to using flow-through cells having a stack of electrodes connected in a bipolar manner. Suitable anode materials are graphite, vitreous carbon, platinum or stainless steel; graphite anodes are preferred. The cathode material is not critical. Use may be made of all conventional metals such as, for example, steel, stainless steel, nickel, titanium, copper, platinum and also graphite or vitreous carbon; graphite or stainless steel are preferred.

The process of the invention is carried out at current densities in the range from 10 to 250 mA/cm², preferably in the range from 25 to 150 mA/cm² and particularly preferably in the range from 40 to 100 mA/cm².

The electrolysis is generally carried out at temperatures between 0° and 80° C.; a preferred temperature range is between 20° and 50° C.

The reaction products obtained are a mixture of 2,2'-dimethyl-1,1'-binaphthyl and 2,7'-dimethyl-1,1'-binaphthyl in a combined yield of about 80%; in addition there are formed about 15% of unknown products, presumably further isomeric dimethylbinaphthyls and about 5% of resin.

The process gives the product in improved power and material yields and avoids the formation of interfering deposits on the electrodes.

It is particularly advantageous that expensive intermediates such as 1-bromo-2-methylnaphthalene and problematical wastes are avoided and the isolation of the product, and also the recycling of unreacted raw material, solvents and electrolyte salts is possible by simple means. In addition, the new process represents, for the first time, an opportunity of preparing 2,7'-dimethyl-1,1'-binaphthyl.

The electrochemical reaction of 2-methylnaphthalene to give dimethylbinaphthyl produces a reaction mixture from which, after separating off water, electrolyte salt, acetonitrile and toluene, it is possible to separate off a narrow-boiling mixture which contains as main component the target compound A 2,2'-dimethyl-1,1'-binaphthyl in a concentration of 52% and 2,3'-dimethyl-1,1'-binaphthyl in a concentration of 33% as secondary component B, besides further isomers and other impurities.

It is known that isomeric mixtures cannot generally be separated using the same process. For example, the isomers m- and p-dichlorobenzene are separated by extractive distillation (U.S. Pat. No. 5,152,875), the isomers o- and p-nitrochlorobenzene by a combined process of melt crystallization and rectification (Przem., Chem., 62 (5), 290 to 292 (1983)), the isomers o- and p-xylene by crystallization and the isomers cis- and trans-decalin by rectification.

The use of rectification for the highly viscous, relatively nonvolatile mixture seemed to have little promise at the beginning because of the danger of thermal decomposition.

Surprisingly, it has now been found that the materials A and B can be separated in the specified order from the other components of the mixture, which were found to be higher-boiling impurities, by rectification under reduced pressure at boiling temperatures of up to 400° C., in particular up to 350° C., without appreciable material losses.

It has been found to be useful to use from 30 to 90, in particular from about 40 to 80, preferably from about 50 to 70, separation stages.

The top pressure is advantageously set at from 5 to 100 hPa, in particular from 10 to 80 hPa, preferably from 10 to 60 hPa.

For the runback ratio, values between 3 and 60 have been found to be useful.

EXAMPLES 1 TO 16

A glass beaker cell of 100 ml capacity provided with a cooling jacket and a magnetic stirrer bar is used. The anode used is a plate of graphite (immersed area 8 cm²); the cathode used is a coarse mesh of stainless steel (immersed area 8 cm²; mesh opening 2 mm, wire thickness 1 mm). The electrodes are vertical and are arranged parallel to one another at a spacing of about 5 mm.

The electrolyte mixtures described in Table 1 are used. Electrolysis is carried out at a temperature of 20° C. and a current of 0.4 A while stirring up to the specified charge amount Q, for which the specified potential U is required. After electrolysis, the electrolysis mixture is evaporated and the residue is taken up in 25 ml of toluene and filtered. The composition of the filtrate is determined by means of gas chromatography; the conversion calculated therefrom and the conversion-based material yield of 2,2'-dimethyl-1,1'-binaphthyl (2,2'-DMBN) and 2,7'-dimethyl-1,1'-binaphthyl (2,7'-DMBN) respectively are likewise shown in Table 1.

Examples 1 to 16: Table 1

| No. | 2-Methyl-napth. (g) | ACN (g) | Water-immiscible component/(g) | $H_2O$ (g) | Electrolyte salt (g) | U (V) | Charge (Ah) | Conversion (%) | 2,2'-DMBN (%) | 2,7'-DMBN (%) |
|---|---|---|---|---|---|---|---|---|---|---|
| 1 | 5.7 | 19.5 | n-heptane/17 | 4 | $NaBF_4$/0.5 | 5–6 | 1.18 | 68 | 50 | 33 |
| 2 | 10 | 19.5 | cyclohexane/19.5 | 4 | $NaBF_4$/0.5 | 7–9 | 1.32 | 59 | 40 | 26 |
| 3 | 10 | 19.5 | toluene/8.6 | 4 | $NaBF_4$/0.5 | 9–12 | 1.32 | 63 | 49 | 33 |
| 4 | 10 | 19.5 | o-xylene/8.9 | 4 | $NaBF_4$/0.5 | 18–20 | 1.32 | 58 | 46 | 31 |
| 5 | 10 | 19.5 | methyl isobutyl ketone/8 | 4 | $NaBF_4$/0.5 | 12–13 | 1.32 | 56 | 47 | 31 |
| 6 | 10 | 19.5 | dichloromethane/13.3 | 4 | $NaBF_4$/0.5 | 14–16 | 1.32 | 52 | 44 | 29 |
| 7 | 10 | 19.5 | t-butyl methyl ether/18.5 | 4 | $NaBF_4$/0.5 | 9–11 | 1.32 | 43 | 42 | 28 |
| 8 | 10 | 19.5 | none (comparative example) | 4 | $NaBF_4$/0.5 | 12–37 | 1.13 | 32 | 35 | 24 |
| 9 | 10 | 19.5 | toluene/8.6 | 4 | $Et_4N\ BF_4$/0.5 | 10–12 | 1.32 | 63 | 50 | 33 |
| 10 | 10 | 19.5 | toluene/8.6 | 4 | $Bu_4N\ BF_4$/0.5 | 13–14 | 1.32 | 55 | 50 | 33 |
| 11 | 10 | 19.5 | toluene/8.6 | 4 | $Bu_4N\ PF_6$/1.0 | 9–10 | 1.32 | 58 | 48 | 32 |
| 12 | 10 | 19.5 | toluene/8.6 | 4 | $Bu_4N\ HSO_4$/1.0 | 12–13 | 1.32 | 26 | 47 | 31 |
| 13 | 10 | 19.5 | toluene/8.6 | 4 | p-$CH_3$—$C_6H_4$—$SO_3\ Et_4N$/1.0 | 14–17 | 1.32 | 42 | 48 | 32 |
| 14 | 10 | 19.5 | toluene/8.6 | 4 | p-Cl—$C_6H_4$—$SO_3\ Et_4N$/1.0 | 10–13 | 1.32 | 55 | 52 | 33 |
| 15 | 10 | 19.5 | toluene/8.6 | 4 | $CH_3SO_3\ Et_4N$/1.0 | 20–22 | 1.32 | 61 | 46 | 30 |
| 16 | 10 | 19.5 | toluene/6.6 | 4 | $CF_3$—CHF—$CF_2$—$SO_3$ Na/1.5 | 20–21 | 1.32 | 61 | 48 | 32 |

EXAMPLE 17

The electrolysis cell used comprises a cylindrical glass vessel (height 150 mm, internal diameter 70 mm) which is provided with a cooling jacket. The anode used is a plate of graphite (width 55 mm, height 110 mm); the cathode used is a coarse mesh of stainless steel (width 55 mm, height 110 mm; mesh opening 2 mm, wire thickness 1 mm). The electrodes are arranged parallel to one another at a mutual spacing of from 5 to 6 mm and are fixed vertically to a holder of polyethylene on the removable cover of the cell. The electrode area immersed in the electrolyte is about 40 $cm^2$. The electrolyte is agitated by means of a magnetic stirrer bar (length 50 mm).

The electrolyte used is a mixture comprising 50 g 2-methylnaphthalene 100 g acetonitrile 43 g toluene 20 g water 2.5 g sodium tetrafluoroborate.

Electrolysis is carried out while stirring at a current density of 30 mA/$cm^2$ and at a temperature of from 20° to 25° C. up to a charge throughput of 8.40 ampere hours. After electrolysis is complete, the electrolysis mixture is separated in a separating funnel, the upper phase (170 g) is evaporated on a rotary evaporator and the residue is distilled under reduced pressure.

This gives 43.5 g of distillate comprising 41% of 2,2'-dimethyl-1,1'-binaphthyl, 25% of 2,7'-dimethyl-1,1'-binaphthyl, 10% of other products and also 24% of unreacted starting material and 4.6 g of distillation residue (resin).

The conversion-based material yield of 2,2'-dimethyl-1, 1'-binaphthyl is 45% and that of 2,7'-dimethyl-1,1'-binaphthyl is 28%. The corresponding current yields are 40% and 24% respectively.

EXAMPLE 18

An undivided, bipolar electrolysis cell having a stack comprising 4 graphite plates (150×160×8 mm) is used. The electrode spacing is 1.5 mm, the anode and cathode areas are each a total of 720 $cm^2$. The cell is operated as a flow-through cell in a circulation apparatus comprising a centrifugal pump and a container, provided with a cooling coil, for the electrolyte.

Electrolysis mixture:

2500 ml acetonitrile 1000 ml toluene 400 ml water 50 g tetraethylammonium tetrafluoroborate 1000 g 2-methylnaphthalene, 98% pure (10.56 mol)

The mixing of the starting components is carried out in the circulation apparatus with gentle pumping. The two-phase electrolysis mixture is then pumped around at a rate of 1500 l/h and electrolysis is carried out at a current of 10.7 amperes, corresponding to a current density of 45 mA/$cm^2$, up to a charge amount of 94 ampere hours. Electrolysis is subsequently continued at a current of 6 amperes up to a charge amount of 150.7 ampere hours. The temperature is maintained at from 20° to 25° C. by cooling. The cell potential is, adhering to the specified electrode spacing and a current of 10.7 amperes, about 20 volts, corresponding to about 6.5 volts per electrode pair. During electrolysis, about 60 l of gas (hydrogen) are evolved.

Workup

After electrolysis is complete, the electrolysis mixture is separated in a separating funnel. The lower phase (350 g), comprising water, acetonitrile and part of the electrolyte salt, is used for the next batch. The upper phase (3850 g) is subjected to distillation under reduced pressure, giving as distillate a mixture of acetonitrile and toluene which is likewise used for the next batch. The distillation residue (1070 g) is stirred with 2500 ml of toluene until the electrolyte salt is completely precipitated, the precipitated electrolyte salt is filtered off on a suction filter and is washed with a little toluene. The filter residue (35 g) comprises recyclable electrolyte salt.

The filtrate is evaporated on a rotary evaporator under reduced pressure and the residue is subsequently subjected to distillation. The first fraction (350 g) distills at from about 60° to 160° C./0.1 mbar and comprises about 98 to 99%-pure, recyclable 2-methylnaphthalene, the main fraction (610 g) distills at from about 160° to 170° C./0.1 mbar and comprises an oil which on cooling to room temperature solidifies to give a vitreous mass and has the following composition, determined by gas chromatography:

about 51% w/w 2,2'-dimethyl-1,1'-binaphthyl (material yield 48%)

about 33% w/w 2,7'-dimethyl-1,1'-binaphthyl (material yield 31%)

about 16% w/w other isomers $^{13}$C-NMR data for 2,7'-dimethyl-1,1'-binaphthyl (100 MHz, CDCl$_3$):

δ ($^{13}$C)ppm: 136.8, 136.35, 135.82, 134.34, 133.54, 132.75, 132.03, 132.02, 128.59, 128.17, 128.12, 127.86, 127.69, 127.42, 127.34, 126.36, 125.82, 124.76, 124.76, 124.76, 124.70, 21.78, 20.57;

EXAMPLE 19

Comparative example as described in Tabuchi et al., Memoirs of the Niihama College of Technology Science and Engineering, 25, 59 (1989), Table 1, Line 1.

Use is made of:

2.84 g 2-methylnaphthalene 70.2 g acetonitrile 10.0 g water 5.3 g LiClO$_4$ 0.804 Ampere hours This gives:

0.88 g of dimer mixture, corresponding to 31% based on the 2-methylnaphthalene used. The dimer mixture comprises, according to GC, at least 5 components including about 50% of 2,2'-dimethyl-1,1'-binaphthyl. During electrolysis, there is precipitated from the electrolyte a dark brown solid which deposits on the anode in particular.

Examples of Rectification

The apparatus comprises a column packed with Sulzer packing of the EX type, a column head comprising reflux condenser and liquid divider, and a vaporizer formed of a round-bottom flask and an electrical heating mantle. Using fitted heating sleeves, heat losses from the flask, the column and the column head can be largely avoided. In the column head, vapor flows into the condenser from below and the condensate produced, which runs back, is divided by means of a magnetically actuated rocking funnel into runback R and distillate D. The boiling of the liquid phase is aided by a magnetic stirrer (Diagram 1).

Rectification Example 1

Rectification using a column DN 30/H 1000 packed with Sulzer-EX

The experiment is carried out using a column of diameter DN=30 mm and an effective separating height H=1000 mm. 730.21 g of isomer mixture are introduced into the flask (V=1 l) and fractional rectification is carried out at pressures of 10 and 20 hPa, in each case measured at the column head, and at runback ratios of initially 10, then 20, 5, 15 and finally 10 again, so that 18 distillate fractions having a total mass of 622.06 g and residues having a total mass of 108.15 g, of which 72.83 g are in the flask and 35.32 g are retained in the column, are produced.

At a pressure of first 10 hPa at the top of the column, a small preliminary fraction and 13 further distillate fractions are taken off. 49.7% of the initial charge are thus separated off as distillate. The temperatures measured vary between 225° and 229° C. in the vapor at the top and between 275° and 277° C. in the liquid phase in the flask.

At a pressure of 20 hPa, 5 further fractions are produced, with a total of a further 35.8% of the initial charge being separated off. The temperature rise to 240° C. in the vapor at the top and to 316.6° C. in the liquid phase in the flask.

The vapor loading factor established during the experiment is between 0.7 and 1.5 (m/s)(kg/m$^3$)$^{1/2}$. The number of separation stages achieved is about 20.

The results of this experiment are summarized in Table 1.

TABLE 1

Rectification of dimethylbinaphthyl isomer mixture in a column packed with DN 30/H 1000 Sulzer laboratory packing of the EX type

| Fraction No. | Pressure | Temperature/°C. Liquid phase in flask | Top | R/D | Distillate fraction mass/g | F$_v$ | % A | % B |
|---|---|---|---|---|---|---|---|---|
| 0 | 7.18 | 273.8 | 220.6 | 10 | 21.17 | — | 90.38 | 8.97 |
| 1 | 9.19 | 274.6 | 225.5 | 10 | 19.47 | 1.05 | 91.83 | 7.74 |
| 2 | 9.20 | 273.8 | 226.6 | 10 | 28.29 | 1.05 | 90.70 | 9.31 |
| 3 | 10.29 | 274.1 | 229.6 | 20 | 36.50 | 0.98 | 91.36 | 8.17 |
| 4 | 10.10 | 274.1 | 229.5 | 20 | 39.09 | 1.06 | 91.00 | 8.16 |
| 5 | 10.04 | 275.5 | 229.9 | 5 | 30.59 | 1.11 | 89.32 | 10.19 |
| 6 | 10.03 | 274.8 | 230.0 | 5 | 30.45 | 1.11 | 85.64 | 13.62 |
| 7 | 9.64 | 274.8 | 229.3 | 5 | 30.75 | 1.14 | 82.24 | 16.84 |
| 8 | 9.05 | 274.8 | 229.5 | 15 | 24.84 | 1.08 | 79.93 | 19.12 |
| 9 | 9.26 | 276.1 | 229.3 | 15 | 24.45 | 1.05 | 81.53 | 17.61 |
| 10 | 10.09 | 277.3 | 229.0 | 15 | 24.29 | 1.17 | 81.09 | 18.11 |
| 11 | 10 | 277 | 229.0 | 15 | 23.78 | 0.96 | 75.29 | 20.79 |
| 12 | 9.3 | 273.8 | 227.7 | 10 | 28.30 | 0.75 | 75.31 | 23.69 |
| 13 | 19 | 275.3 | 236.9 | 10 | 15.89 | 0.47 | 69.69 | 29.15 |
| 14 | 19 | 274.0 | 239.6 | 10 | 19.84 | 0.48 | 58.75 | 39.61 |
| 15 | 22 | 271.3 | 219.7 | 10 | 34.25 | 0.76 | 38.75 | 58.62 |
| 16 | 20 | 283.1 | 214.1 | 10 | 120.37 | 1.20 | 10.36 | 81.16 |
| 17 | 20 | 316.6 | 128.5 | 10 | 69.74 | 0.73 | 0.93 | 72.00 |
| Products | | | | | 622.06 g 109.15 g 730.21 g | | | |

TABLE 1-continued

Rectification of dimethylbinaphthyl isomer mixture in a column packed with DN 30/H 1000 Sulzer laboratory packing of the EX type

| Residue | | % A | % B | Feed: | | % A | % B |
|---|---|---|---|---|---|---|---|
| in flask: | 72.83 g | <0.1 | 10.23 | in flask: | 727.85 g | 50.73 | 36.30 |
| in column: | 35.32 g | <0.1 | 10.23 | Loss: | 2.26 | | |
| | | | | and | 0.32% | | |

R = Runback amount (g/h)
D = Distillate amount (g/h)
$F_v$ = Vapor loading factor $[(m/s) \sqrt{(kg/m^3)}]$

Rectification Example 2

Rectification using a column DN 50/H 2000 packed with Sulzer EX

This experiment is carried out using a column having a diameter DN=50 mm and an effective separating height of H=2000 mm. The flask having a volume of 4 l is charged with 3000.74 g of isomer mixture and fractional rectification is carried out at a constant top pressure of 20 hPa and a runback ratio of initially 20, then 40, 10, 60 and finally 30, so that 26 distillation fractions having a total mass of 2431.0 g and residues having a total mass of 570 g, of which 420 g are in the flask, 120 g are retained in the column and 30 g are in liquid-phase and residue samples, are produced. During the course of the separation, the temperature in the boiling liquid phase in the flask rises from 285° to 350° C. and in the vapor at the top from 243° to 253° C. The rectification is interrupted twice, with the liquid phase in the flask being transferred to a smaller flask having a volume of 2 l during the first break.

The vapor loading factor established during the experiment is between 0.7 and 1.6 $(m/s)(kg/m^3)^{1/2}$. The number of separation stages achieved is about 40.

The results of this experiment are summarized in Table 2.

TABLE 2

Rectification of dimethylbinaphthyl isomer mixture in a column packed with DN 50/H 2000 Sulzer laboratory packing of the EX type

| Fraction No. | Pressure | Temperature/°C. Liquid phase in flask | Top | R/D | Distillate fraction mass/g | $F_v$ | % A | % B |
|---|---|---|---|---|---|---|---|---|
| 0 | 19.9 | 285.1 | 242.6 | 20 | 46.3 | — | 89.21 | 0.51 |
| 1 | 20.0 | 288.2 | 246.6 | 20 | 149.1 | 0.82 | 99.18 | 0.37 |
| 2 | 20.0 | 289.9 | 246.3 | 20 | 168.8 | 0.69 | 99.71 | 0.22 |
| 3 | 20.0 | 289.9 | 246.4 | 20 | 171.3 | 0.70 | 99.71 | 0.25 |
| 4 | 20.0 | 290.8 | 250.7 | 20 | 200.5 | 1.66 | 99.60 | 0.40 |
| 5 | 20.0 | 289.9 | 246.6 | 20 | 122.2 | 0.59 | 99.15 | 0.84 |
| 6 | 20.0 | 290.4 | 246.6 | 20 | 183.6 | 1.51 | 98.98 | 0.79 |
| 7 | 19.9 | 290.9 | 246.3 | 20 | 105.3 | 1.48 | 98.19 | 1.51 |
| 8 | 20.0 | 290.8 | 246.4 | 40 | 92.0 | 1.61 | 97.17 | 2.50 |
| 9 | 20.0 | 288.1 | 245.4 | 40 | 89.7 | 1.44 | 96.04 | 3.55 |
| 10 | 20.0 | 286.7 | 245.8 | 40 | 80.6 | 1.29 | 92.54 | 6.98 |
| 11 | 19.8 | 287.0 | 247.3 | 40 | 82.1 | 1.33 | 81.82 | 17.44 |
| 12 | 20.0 | 286.5 | 249.4 | 40 | 73.8 | 1.19 | 60.35 | 38.68 |
| 13 | 19.9 | 287.5 | 250.7 | 40 | 77.5 | 1.25 | 34.47 | 64.31 |
| 14 | 20.2 | 275 | 251.8 | 40 | 15.1 | — | 26.31 | 72.30 |
| 15 | 19.8 | 285 | 252.1 | 40 | 70.1 | 0.57 | 17.41 | 84.10 |
| 16 | 19.8 | 285 | 252.4 | 40 | 106.5 | 1.18 | 5.68 | 92.97 |
| 17 | 19.8 | 285 | 252.1 | 40 | 85.9 | 0.98 | 1.74 | 96.54 |
| 18 | 20.2 | 285 | 253.1 | 40 | 31.3 | 0.75 | 0.97 | 97.14 |
| 19 | 20.2 | 285 | 253.1 | 10 | 142.4 | 1.23 | 0.44 | 97.03 |
| 20 | 20.2 | 285 | 253.1 | 10 | 129.3 | 1.12 | 0.70 | 94.45 |
| 21 | 20.0 | 285 | 252.8 | 60 | 23.3 | 0.84 | 1.76 | 90.95 |
| 22 | 19.9 | 290 | 252.1 | 60 | 50.1 | 0.90 | — | 91.87 |
| 23 | 20.0 | 310 | 252.4 | 60 | 66.6 | 0.80 | — | 89.20 |
| 24 | 19.9 | 350 | 252.7 | 30 | 59.6 | 0.73 | — | 63.95 |
| 25 | | | further fraction | 30 | 8.0 | | — | 78.99 |
| | | | | | 2431.0 g | | | |

| Residue | | % A | % B | Feed: | | % A | % B |
|---|---|---|---|---|---|---|---|
| in flask: | 421 g | 0 | 11.65 | in flask: | 3000.74 g | 52.12 | 32.98 |
| in column: | 128 g | 0 | 11.65 | | | | |
| 2 Samples: | 20 g | | | | | | |

We claim:

1. Amended) A process for preparing 2,2'-dimethyl-1,1'-binaphthyl, 2,7'-dimethyl-1,1'-binaphthyl, or mixtures thereof, which comprises the steps of electrochemically oxidatively dimerizing 2-methyl-naphthalene in the presence of an electrolyte which comprises a mixture of acetonitrile, water, and an electrolyte salt, which additionally contains at least one further component which is immiscible or only partially miscible with water, and rectifying the reaction mixture obtained under reduced pressure.

2. The process as claimed in claim 1, wherein the water-immiscible component is an aliphatic or cycloaliphatic hydrocarbon, an aromatic hydrocarbon, a halogenated hydrocarbon; a ketone or a mixture thereof.

3. The process as claimed in claim 2, wherein the aliphatic or cycloaliphatic hydrocarbon is pentane, hexane, cyclohexane, methylcyclohexane, heptane, octane, isooctane, decane, dodecane or decalin.

4. The process as claimed in claim 2, wherein the aromatic hydrocarbon is benzene, toluene, o-, m-, or p-xylene, mesitylene, naphthalene or tetralin.

5. The process as claimed in claim 2, wherein the halogenated hydrocarbon is methylene chloride or chlorobenzene.

6. The process as claimed in claim 2, wherein the ketone contains from 5 to 10 carbon atoms.

7. The process as claimed in claim 2, wherein the aliphatic or cycloaliphatic hydrocarbon has from 6 to 10 carbon atoms.

8. The process as claimed in claim 2, wherein the aliphatic or cycloaliphatic hydrocarbon is heptane or octane.

9. The process as claimed in claim 2, wherein the aromatic hydrocarbon has from 6 to 10 carbon atoms.

10. The process as claimed in claim 2, wherein the aromatic hydrocarbon is toluene or xylene.

11. The process as claimed in claim 2, wherein the ketone is diethyl ketone, methyl tert-butyl ketone, or acetophenone.

12. The process as claimed in claim 1, wherein the electrochemically oxidatively dimerizing is done by electrolysis.

13. The process as claimed in claim 12, wherein the further component which is water-immiscible comprises 2-methylnaphthalene.

14. The process as claimed in claim 13, wherein the concentration of 2-methylnaphthalene during electrolysis is from 10 to 50 % by weight based on the total weight of the electrolyte.

15. The process as claimed in claim 13, wherein the concentration of 2-methylnaphthalene during electrolysis is from 15 to 40 % by weight based on the total weight of the electrolyte.

16. The process as claimed in claim 12, wherein the electrolysis is carried out at current densities of from 10 to 250 mA/cm$^2$.

17. The process as claimed in claim 12, wherein the electrolysis is carried out at temperatures from 0° to 80° C.

18. The process as claimed in claim 12, wherein the electrolysis is carried out at current densities of from 25 to 150 mA/cm$^2$.

19. The process as claimed in claim 12, wherein the electrolysis is carried out at current densities of from 40 to 100 mA/cm$^2$.

20. The process as claimed in claim 12, wherein the electrolysis is carried out at temperatures of from 20° to 50° C.

21. The process as claimed in claim 12, wherein the electrolysis is conducted in a two-layer system.

22. The process as claimed in claim 1, wherein the electrolyte salt used is an alkali metal, alkaline earth metal, ammonium, monoalkylammonium, dialkylammonium, trialkylammonium or tetraalkylammonium salt of acids whose anions are from a 6-valent sulfur, 5-valent phosphorus or 3-valent boron, or mixtures thereof.

23. The process as claimed in claim 22, wherein the anions used are hydrogen sulfate, methyl sulfate, ethyl sulfate, methanesulfonate, ethanesulfonate, propanesulfonate, butanesulfonate, octanesulfonate, benzenesulfonate, toluenesulfonate, 2-chlorobenzenesulfonate, p-chlorobenzenesulfonate, 2,4-dichlorobenzenesulfonate, naphthalene-1-sulfonate, naphthalene-2-sulfonate, methanephosphonate, ethanephosphonate, propanephosphonate, butanephosphonate, hexafluorophosphate, tetrafluoroborate or mixtures thereof.

24. The process as claimed in claim 1, wherein the electrolyte salt used is a salt of an alkanesulfonic acid or acids or alkanephosphonic acids whose alkyl radical is polyfluorinated or perfluorinated.

25. The process as claimed in claim 1, wherein the weight ratio of acetonitrile to water is from 100:1 to 1:1.

26. The process as claimed in claim 1, wherein the amount of the component which is immiscible or only partially miscible with water is from 10 to 90% based on the total weight of the electrolyte.

27. The process as claimed in claim 1, wherein the amount of the electrolyte salt is from 0.5 to 15% by weight based on the total weight of the electrolyte.

28. The process as claimed in claim 1, wherein the dimerizing is carried out using an anode which is graphite, vitreous carbon, platinum or stainless steel.

29. The process as claimed in claim 28, wherein the anode used is graphite.

30. The process as claimed in claim 1, wherein the dimerizing is carried out using a cathode which is graphite, vitreous carbon, or a metal.

31. The process as claimed in claim 30, wherein the cathode used is graphite or vitreous carbon.

32. The process as claimed in claim 1, wherein the rectification is carried out at boiling temperatures of up to 400° C.

33. The process as claimed in claim 1, wherein the rectification is carried out using from 30 to 90 separation stages.

34. The process as claimed in claim 1, wherein the rectification is carried out at a top pressure of from 5 to 100 hPa.

35. The process as claimed in claim 1 wherein the rectification is carried out at runback ratios between 3 and 60.

36. The process as claimed in claim 1, wherein the electrolyte salt used is trifluoromethanesulfonate, 1,1,2,3,3,3-hexafluoropropanesulfonate, nonafluorobutanesulfonate, heptadecafluorooctanesulfonate, trifluoromethanephosphonate, or nonafluorobutanephosphonate.

37. The process as claimed in claim 1, wherein the weight ratio of acetonitrile to water is from 20:1 to 2:1.

38. The process as claimed in claim 1, wherein the amount of the further component which is immiscible or only partially miscible with water is from 20 to 80 % based on the total weight of the electrolyte.

39. The process as claimed in claim 1, wherein the amount of the electrolyte salt is from 1 to 7 % by weight based on the total weight of the electrolyte.

40. The process as claimed in claim 1, wherein the rectification is carried out at boiling temperatures of up to 350° C.

41. The process as claimed in claim 1, wherein the rectification is carried out using from 40 to 80 separation stages.

42. The process as claimed in claim 1, wherein the rectification is carried out using from 50 to 70 separation stages.

43. The process as claimed in claim 1, wherein the rectification is carried out at a top pressure of from 10 to 80 hPa.

44. The process as claimed in claim 1, wherein the rectification is carried out at a top pressure of from 10 to 60 hPa.

45. The process as claimed in claim 1, wherein the electrolyte salt used is (a) sodium salt, (b) tetraalkylammonium salt having alkyl radicals containing from 1 to 4 carbon atoms of alkanesulfonic acids wherein said alkane is an alkyl radicals containing from 1 to 8 carbon atoms, (c) tetraalkylammonium salt having alkyl radicals containing from 1 to 4 carbon atoms of alkanesulfonic acids wherein said alkane is a polyfluorinated alkyl radical containing from 1 to 4 carbon atoms, (d) tetraalkylammonium salt having alkyl radicals containing from 1 to 4 carbon atoms of alkanesulfonic acids wherein said alkane is a perfluorinated alkyl radical containing from 1 to 4 carbon atoms, (e) tetraalkylammonium salt having alkyl radicals containing from 1 to 4 carbon atoms of of arylsulfonic acids, wherein the aryl is phenyl, naphthyl; alkyl-substituted phenyl or chloro-substituted phenyl, (f) tetraalkylammonium salt having alkyl radicals containing from 1 to 4 carbon atoms of tetrafluoroboric acid or (g) tetraalkylammonium salt having alkyl radicals containing from 1 to 4 carbon atoms of hexafluorophosphoric acid.

* * * * *